(12) United States Patent
Chen et al.

(10) Patent No.: US 7,770,776 B2
(45) Date of Patent: Aug. 10, 2010

(54) ROTATABLE STAPLING HEAD OF A SURGICAL STAPLER

(75) Inventors: Wang-dong Chen, Suzhou (CN); Quan Chen, Suzhou (CN); Jiang Lin, Suzhou (CN); Ming-yao Lu, Suzhou (CN); Wei-zhong Yin, Suzhou (CN)

(73) Assignee: Suzhou Touchstone International Medical Science Co., Ltd, Suzhou (CN)

( * ) Notice: Subject to any disclaimer, the term of this patent is extended or adjusted under 35 U.S.C. 154(b) by 122 days.

(21) Appl. No.: 11/814,664

(22) PCT Filed: Jun. 29, 2005

(86) PCT No.: PCT/CN2005/000942

§ 371 (c)(1),
(2), (4) Date: Mar. 12, 2008

(87) PCT Pub. No.: WO2006/079260

PCT Pub. Date: Aug. 3, 2006

(65) Prior Publication Data

US 2009/0001127 A1    Jan. 1, 2009

(30) Foreign Application Priority Data

Jan. 26, 2005   (CN)   .................... 2005 2 0068601 U
Jan. 26, 2005   (CN)   .................... 2005 2 0068602 U
Jan. 26, 2005   (CN)   .................... 2005 2 0068603 U
Jan. 26, 2005   (CN)   .................... 2005 2 0068604 U

(51) Int. Cl.
*A61B 17/03*    (2006.01)

(52) U.S. Cl. .................... 227/180.1; 227/179.1; 227/19; 227/176.1; 227/175.1

(58) Field of Classification Search .............. 227/180.1, 227/19, 175.1, 176.1, 179.1
See application file for complete search history.

(56) References Cited

U.S. PATENT DOCUMENTS

| 5,522,534 | A | * | 6/1996 | Viola et al. | 227/179.1 |
| 5,533,661 | A | * | 7/1996 | Main et al. | 227/176.1 |
| 5,609,285 | A | * | 3/1997 | Grant et al. | 227/179.1 |
| 5,673,842 | A | | 10/1997 | Bittner et al. | 227/175.4 |
| 5,829,662 | A | | 11/1998 | Allen et al. | 227/177.1 |
| 5,868,760 | A | * | 2/1999 | McGuckin, Jr. | 606/139 |
| 6,010,054 | A | | 1/2000 | Johnson et al. | 227/176.1 |
| 6,119,913 | A | * | 9/2000 | Adams et al. | 227/176.1 |
| 6,343,731 | B1 | | 2/2002 | Adams et al. | 227/180.1 |
| 6,629,630 | B2 | * | 10/2003 | Adams | 227/180.1 |
| 6,805,273 | B2 | * | 10/2004 | Bilotti et al. | 227/180.1 |
| 6,820,791 | B2 | * | 11/2004 | Adams | 227/180.1 |
| 6,957,758 | B2 | * | 10/2005 | Aranyi | 227/176.1 |

(Continued)

FOREIGN PATENT DOCUMENTS

CN    2557085    6/2003

(Continued)

*Primary Examiner*—Brian D Nash
(74) *Attorney, Agent, or Firm*—Allen, Dyer, Doppelt, Milbrath & Gilchrist, P.A.

(57) ABSTRACT

The present invention provides a rotatable stapling head of a surgical stapler, which comprises a staple cartridge (1), a staple driver (2), a scalpel (3), a compression rod (4), a staple casing (5) and a rotating assembly. The above parts constitute a rotating forward mechanism which can rotatablely forward the scalpel therein.

15 Claims, 10 Drawing Sheets

U.S. PATENT DOCUMENTS 6,959,851 B2 * 11/2005 Heinrich ................ 227/175.1
7,118,528 B1 * 10/2006 Piskun ..................... 600/105
7,210,609 B2 *  5/2007 Leiboff et al. ........... 227/180.1
7,325,713 B2 *  2/2008 Aranyi .................... 227/176.1

FOREIGN PATENT DOCUMENTS

EP          1090592         4/2001

* cited by examiner

ROTATABLE STAPLING HEAD OF A SURGICAL STAPLER

FIELD OF THE INVENTION

The present invention generally relates to a stapling head of a surgical stapler, more particularly, to a rotatable stapling head of a surgical stapler.

BACKGROUND OF THE INVENTION

To perform anastomosis stapling operations, the following methods are used, such as manual sutures by needles, medical adhesive, surgical zip and surgical stapler, etc,. Among which a surgical stapler as a tool for tissue anastomosis is more and more widely used in surgery operations. In the process of anastomosis stapling with a prior art stapling head of a surgical stapler, its annular scalpel moves in beeline which requires much strength from a surgical operator to complete cutting operation, and also it is easily apt to cut the excess tissue around the wound incompletely which is harmful to patient health. Therefore, many improvements on stapling anvil have been made from overseas, such as annular severable anvil, anvil with steps thereon. Alternatively, some improvements are made on the scalpel itself, for example, the edge of scalpel is made in the shape of interval serrations. But in practice, the improvements mentioned above are unable to solve the problems of cutting the excess tissue around the wound incompletely and requiring too much strength.

SUMMARY OF THE INVENTION

The invention is aimed at solving the problems of prior art by providing a rotatable stapling head of a surgical stapler which can cut the unwanted tissue around the wound completely but with less strength from the operator.

The object of the present invention is achieved by the following technical scheme:

A rotatable stapling head of a surgical stapler comprises:

a staple cartridge, a staple driver, a scalpel, a compression rod, a staple casing, and a rotating assembly;

wherein said staple cartridge, staple driver, scalpel, compression rod, staple casing, and rotating assembly constitute a rotating forward mechanism which can rotatablely forward said scalpel therein.

The present invention may be further improved by the following measures:

A rotatable stapling head of a surgical stapler as mentioned above, wherein said rotating assembly includes a rotating sleeve and a spiral track member; said staple cartridge, staple driver, scalpel, compression rod, staple casing, rotating sleeve and spiral track member constitute a rotating forward mechanism which can rotatablely forward said scalpel therein;

and wherein said staple casing is a tubular casing with an inner step shaped cavity inside which is disposed a support tube; a step-shape tubular staple driver, which conforms to the shape of the inner wall of the staple casing, is disposed between the support tube and the inner wall of the staple casing;

and wherein a scalpel cavity is formed in front of the staple casing and the staple driver, which matches the annular scalpel; and the annular scalpel is sleeved outside the support tube and disposed inside the scalpel cavity;

and wherein the front circular rim of the staple casing is connected with the annular staple cartridge and the front circular rim of the staple driver contacts with the annular staple cartridge; and the annular scalpel is connected with the staple driver and the support tube by means of the rotating sleeve;

and wherein the rotating sleeve has therein a concave-convex structure selected from the group consisting of flutes and bosses; the spiral track member is disposed on the support tube inside the staple casing so as to match with the flutes or bosses of the rotating sleeve.

Wherein the rotating sleeve is fixed with the annular scalpel; the spiral track member is a spiral track directly disposed on the support tube; and wherein a hook is disposed at the bottom of the front cavity of the staple driver so as to hook with the bottom of the rotating sleeve; and wherein a slide mechanism is dispose at the bottom of the rotating sleeve, said slide mechanism comprises balls, ball collars and gaskets.

A rotatable stapling head of a surgical stapler as mentioned above, wherein said rotating assembly is a connecting rod assembly; and wherein said staple cartridge, staple driver, scalpel, staple casing, and connecting rod assembly constitute a rotating forward mechanism which can rotatablely forward said scalpel therein; said staple casing is a tubular casing with an inner step shaped cavity inside which is disposed a support tube; a step-shape tubular staple driver, which conforms to the shape of the inner wall of the staple casing, is disposed between the support tube and the inner wall of the staple casing; a scalpel cavity is formed in front of the staple casing and the staple driver, which matches the annular scalpel; the annular scalpel is sleeved outside the support tube and disposed inside the scalpel cavity; and wherein the front circular rim of the staple casing is connected with the annular staple cartridge and the front circular rim of the staple driver contacts with the annular staple cartridge; and the annular scalpel is connected with the staple driver and the support tube by means of the connecting rod assembly. The connecting rod assembly comprises a fastening nut, a rotating sleeve, hinge mounts, connecting rods, a hinge mount sleeve, a fastening bolt; a threaded insert is disposed on a stepped outer wall of the support tube in the annular scalpel; the hinge mount sleeve is disposed on a shoulder of the stepped outer wall of the support tube below the threaded insert; the first hinge mounts are disposed on the hinge mount sleeve; a fastening nut is disposed on the first hinge mounts by means of the threaded insert; the bottom of each of the first hinge mounts is connected movably with one end of one of the connecting rods by means of one of the pins, the other end of the connecting rod is connected movably with one of the second hinge mounts which is disposed in the rotating sleeve that fixed below the front of the staple driver by means of one of the pins.

A rotatable stapling head of a surgical stapler as mentioned above, wherein said rotating assembly is an inclined surface & rotating sleeve assembly; and wherein said staple cartridge, staple driver, scalpel, staple casing, and inclined surface & rotating sleeve assembly constitute a rotating forward mechanism which can rotatablely forward said scalpel therein; said staple casing is a tubular casing with an inner step shaped cavity inside which is disposed a support tube; a step-shape tubular staple driver, which conforms to the shape of the inner wall of the staple casing, is disposed between the support tube and the inner wall of the staple casing; a scalpel cavity is formed in front of the staple casing and the staple driver, which matches the annular scalpel; the annular scalpel is sleeved outside the support tube and disposed inside the scalpel cavity; and wherein the front circular rim of the staple casing is connected with the annular staple cartridge and the front circular rim of the staple driver contacts with the annular staple cartridge; and the annular scalpel is connected with the staple driver and the support tube by means of the inclined surface & rotating sleeve assembly. The inclined surface & rotating sleeve assembly comprises a rotating sleeve and a connecting sleeve; the connecting sleeve is fixed on the support tube in the staple casing with inclined surfaces disposed on its outer wall; the rotating sleeve is hinged with the annular scalpel with inclined surfaces disposed thereon which match with the inclined surfaces disposed on the connecting sleeve; a hook is disposed at the bottom of the front of the staple driver so as to hook with the bottom of the rotating sleeve.

A rotatable stapling head of a surgical stapler as mentioned above, wherein said rotating assembly is a string & rotating sleeve assembly; and wherein said staple cartridge, staple driver, scalpel, staple casing, and string & rotating sleeve assembly constitute a rotating forward mechanism which can rotatablely forward said scalpel therein; said staple casing is a tubular casing with an inner step shaped cavity inside which is disposed a support tube; a step-shape tubular staple driver, which conforms to the shape of the inner wall of the staple casing, is disposed between the support tube and the inner wall of the staple casing; a scalpel cavity is formed in front of the staple casing and the staple driver, which matches the annular scalpel; the annular scalpel is sleeved outside the support tube and disposed inside the scalpel cavity; and wherein the front circular rim of the staple casing is connected with the annular staple cartridge and the front circular rim of the staple driver contacts with the annular staple cartridge; and the annular scalpel is connected with the staple driver and the support tube by means of the string & rotating sleeve assembly. The string & rotating sleeve assembly comprises a rotating sleeve, a string lock, a string and a torsion spring; the rotating sleeve is sleeved outside the support tube and fixed at the outer bottom of the annular scalpel; the upper of the rotating sleeve is connected with the outer wall of the support tube by means of the torsion spring; and the string is disposed below the rotating sleeve with one end of the string fixed at the bottom of the rotating sleeve, and the other end of the string goes through out of the staple casing to be fixed with the string lock; a hook is disposed at the bottom of the front cavity of the staple driver so as to hook with the bottom of the rotating sleeve.

The present invention has following advantages: 1. It enables rotating cutting. 2. It enables active rotating. 3. It reduces anti-force from cutting tissue. 4. It reduces wounds caused by stretching in the process of cutting. 5. It is more safe and stable to cut tissue in surgery operations. 6. It requires less force from the surgical stapler operator.

Further features and advantages of the present invention will become apparent from the following detailed description, in combination with the appended drawings.

DETAILED DESCRIPTION OF THE PREFERRED EMBODIMENTS

Figure 1:
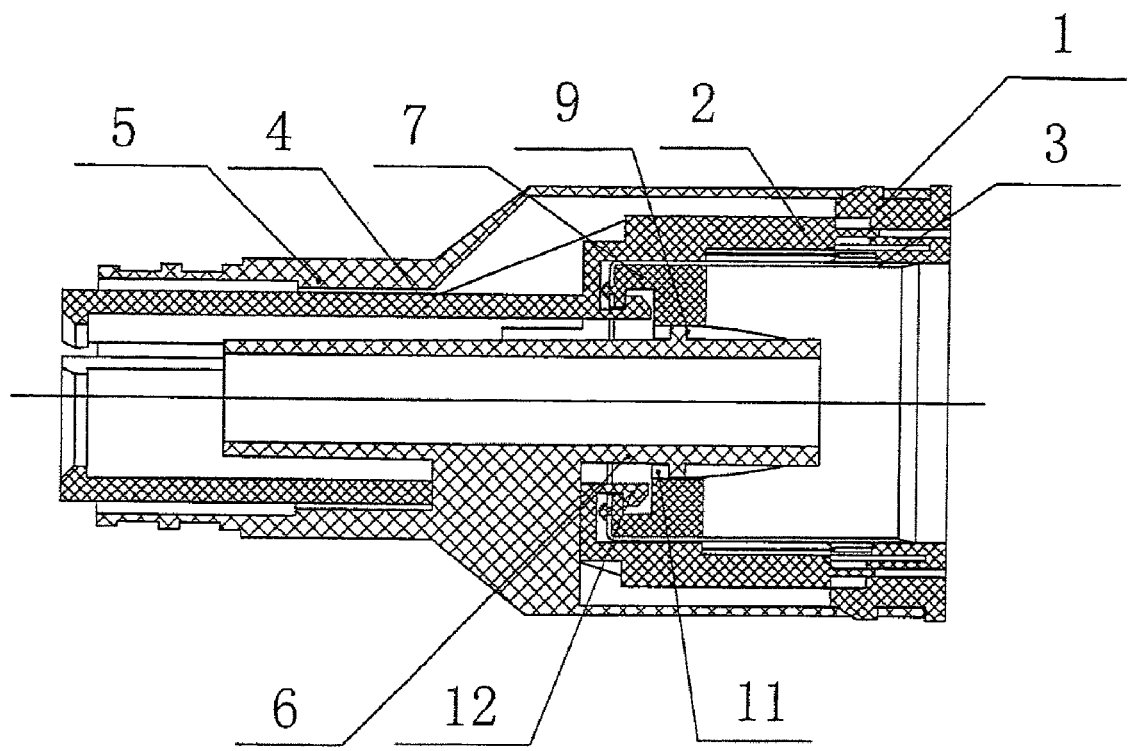
FIG. 1 is a cross-sectional view of a rotatable stapling head with the rotating sleeve disposed inside the scalpel according to one embodiment of the present invention.

As shown in FIGS. 1 to 12, a rotatable stapling head of a surgical stapler of the present invention comprises a staple cartridge 1, a staple driver 2, a scalpel 3, a compression rod 4, a staple casing 5, a rotating sleeve 7 having thereon a concave-convex structure 11 selected from the group consisting of flutes and bosses, a spiral track member inside the staple casing 5 so as to match with the concave-convex structure of the rotating sleeve. Said staple cartridge 1, staple driver 2, scalpel 3, compression rod 4, staple casing 5, rotating sleeve 7 constitute a rotating forward mechanism which can rotatablely forward said scalpel therein. The staple casing 5 is a tubular casing with an inner step shaped cavity inside which is disposed a support tube 6; a step-shape tubular staple driver 2, which conforms to the shape of the inner wall of the staple casing, is disposed between the support tube 6 and the inner wall of the staple casing; and a scalpel cavity is formed in front of the staple casing 5 and the staple driver 2, which matches the annular scalpel; and the annular scalpel 3 is sleeved outside the support tube 6 and disposed inside the scalpel cavity The spiral track member is disposed on the support tube 6 so as to match with the rotating sleeve 7; and the front circular rim of the staple casing 5 is connected with the annular staple cartridge 1 and the front circular rim of the staple driver 2 contacts with the annular staple cartridge 1; and the annular scalpel 3 is connected with the staple driver 2 and the support tube 6 by means of the rotating sleeve 7. The spiral track member is a spiral track 9 directly disposed on the support tube 6; and the rotating sleeve 7 is connected with the support tube 6. Alternatively, the spiral track member is a fixed spiral sleeve 13 with the spiral track 9 disposed on the outer wall thereof, and the fixed spiral sleeve is fixed outside the support tube 6; the support tube 6 has a threaded insert 8 on its front end with a limit fastening nut 10 disposed thereon. When the staple driver 2 is pushed forward, it drives the rotating sleeve 7 and the scalpel 3 to move forward, meanwhile, the concave-convex structure 11 of the rotating sleeve 7 matches with the spiral track 9 so as to drive the rotating sleeve 7 to rotate, accordingly the scalpel rotates along with the rotating sleeve 7. After stapling, the scalpel and the rotating sleeve retract back to the staple casing 5 by the force from the hook 12 which is disposed on the staple driver.

Embodiment 1

Figure 2:
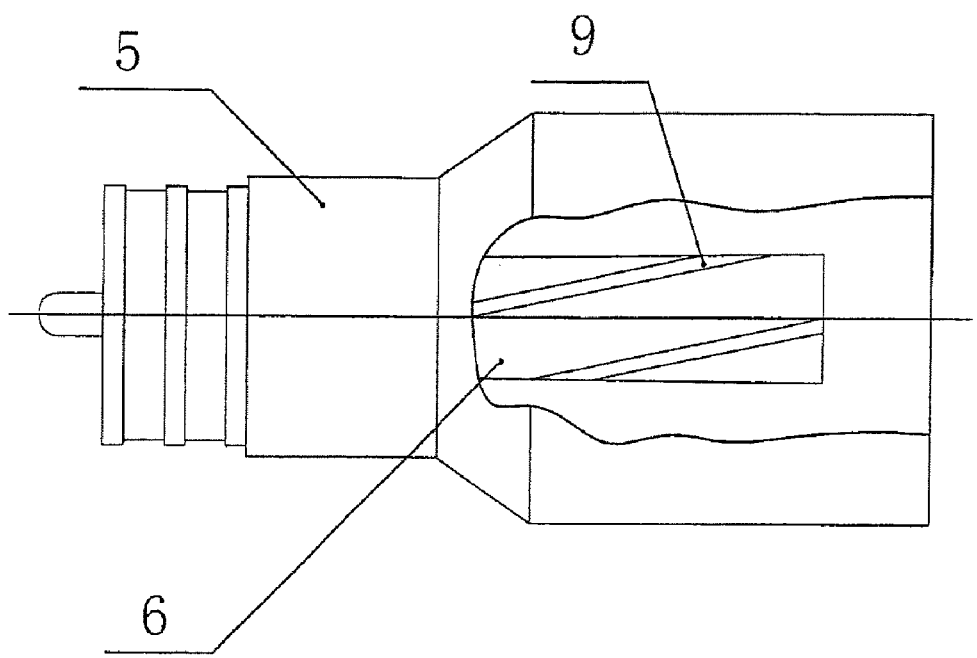
FIG. 2 is a partially cut-off view of the rotatable stapling head as shown in FIG. 1.
Figure 3:
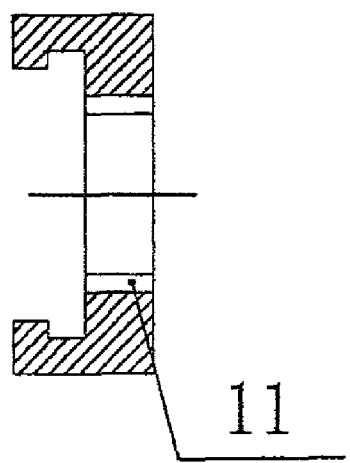
FIG. 3 is a cross-sectional view of the rotating sleeve in the rotatable stapling head as shown in FIG. 1.
Figure 4:
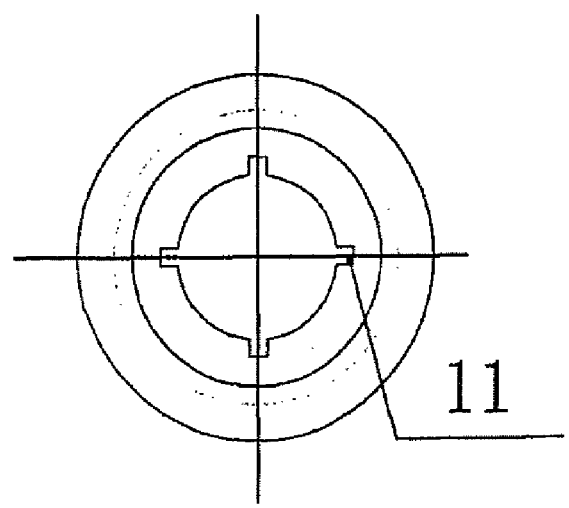
FIG. 4 is a left view of the rotating sleeve as shown in FIG. 3.

As shown in FIGS. 1 and 2, the staple driver 2 and the compression rod 4 are made integral, the rotating sleeve 7 is disposed at the inner bottom of the annular scalpel 3; the hook 12 is disposed at the bottom of the front cavity of the staple driver 2 so as to hook with the bottom of the annular scalpel 3. When the staple driver 2 is pushed forward, it drives the rotating sleeve 7 and the scalpel 3 to move forward, meanwhile, the concave-convex structure 11 of the rotating sleeve 7 matches with the spiral track 9 of the support tube 6 in the staple casing so as to drive the rotating sleeve 7 to rotate. Because the rotating sleeve 7 is riveted with the scalpel 3, the scalpel 3 rotates along with the rotating sleeve 7. After stapling, the scalpel 3 and the rotating sleeve 7 retract back to the staple casing by the force from the hook 12 which is disposed on the staple driver.

Embodiment 2

Figure 5:
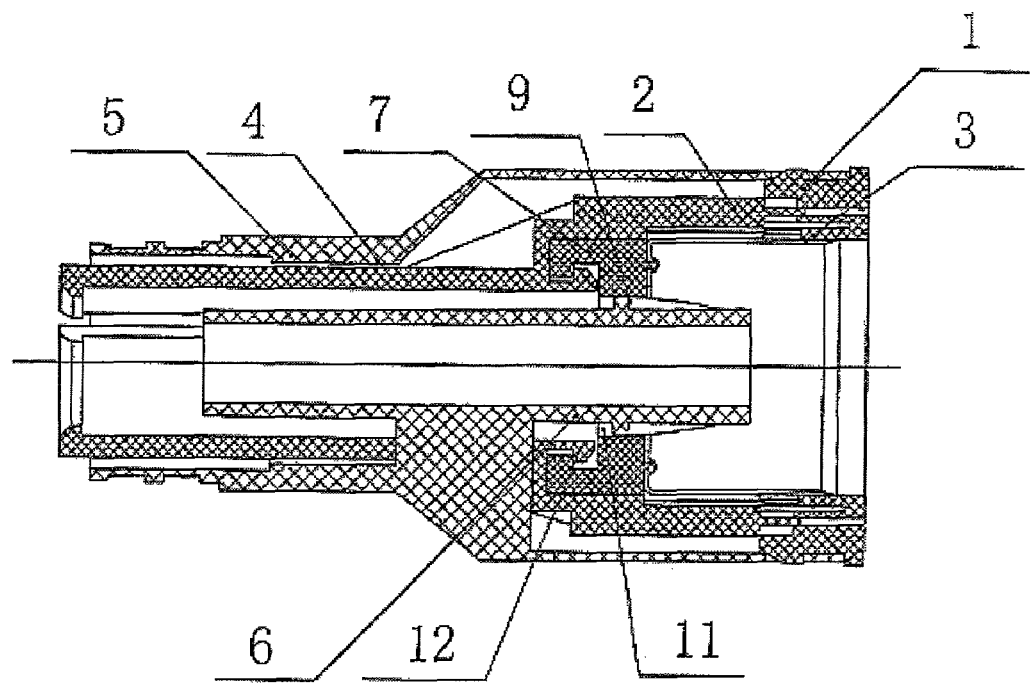
FIG. 5 is a cross-sectional view of a rotatable stapling head with the rotating sleeve disposed outside the scalpel according to another embodiment of the present invention.

As shown in FIG. 5, the staple driver 2 and the compression rod 4 are made integral, the rotating sleeve 7 is disposed at the outer bottom of the annular scalpel 3; the hook 12 is disposed at the bottom of the front cavity of the staple driver 2 so as to hook with the bottom of the rotating sleeve 7. When the staple driver 2 is pushed forward, it drives the rotating sleeve 7 and the scalpel 3 to move forward, meanwhile, the concave-convex structure 11 of the rotating sleeve matches with the spiral track 9 of the support tube 6 in the staple casing so as to drive the rotating sleeve 7 to rotate. Because the rotating sleeve 7 is riveted with the scalpel 3, the scalpel 3 rotates along with the rotating sleeve 7. After stapling, the scalpel 3 and the rotating sleeve 7 retract back to the staple casing by the force from the hook 12 which is disposed on the staple driver.

Embodiment 3

Figure 6:
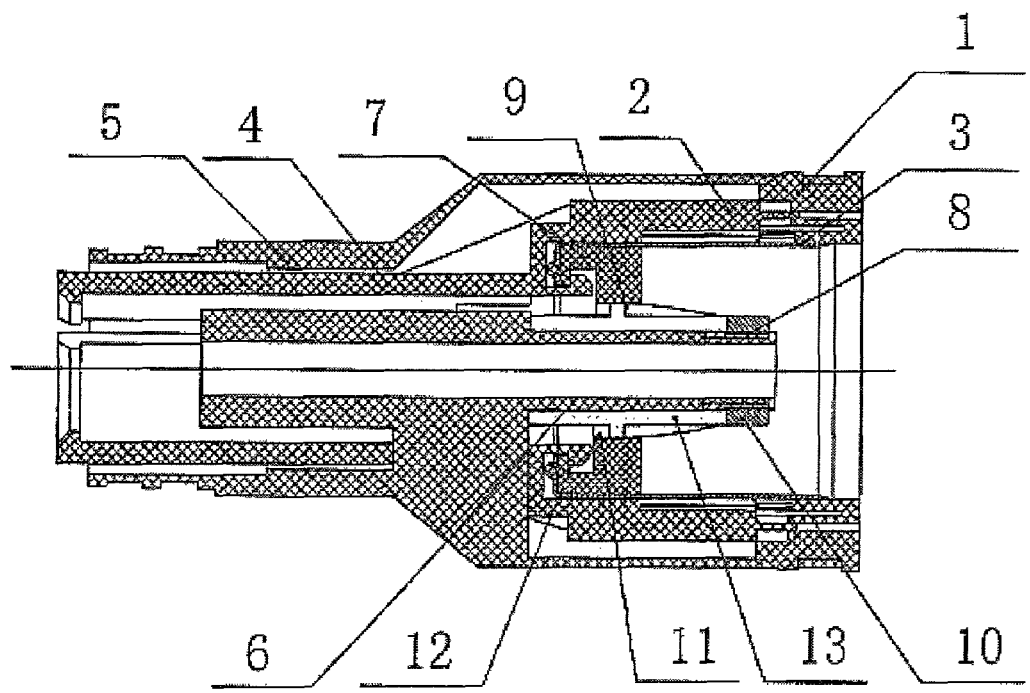
FIG. 6 is a cross-sectional view of a rotatable stapling head employing a spiral track member according to another embodiment of the present invention.
Figure 7:
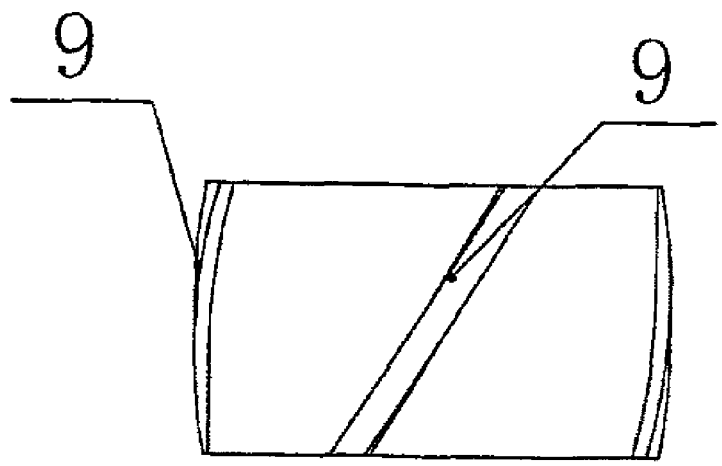
FIG. 7 is a schematic view of the fixed spiral sleeve in the rotatable stapling head as shown in FIG. 6.
Figure 8:
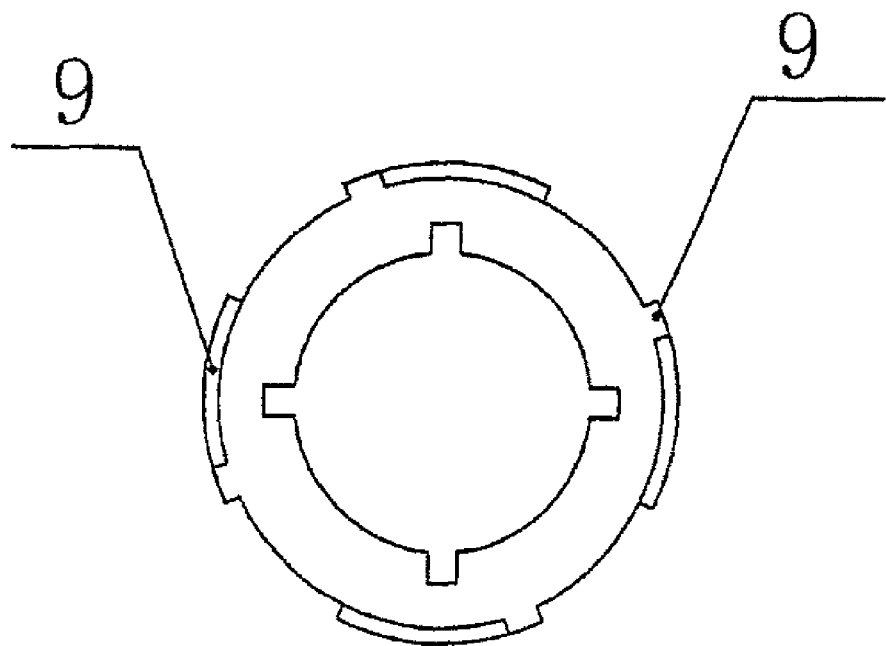
FIG. 8 is a top view of the fixed spiral sleeve as shown in FIG. 7.
Figure 9:
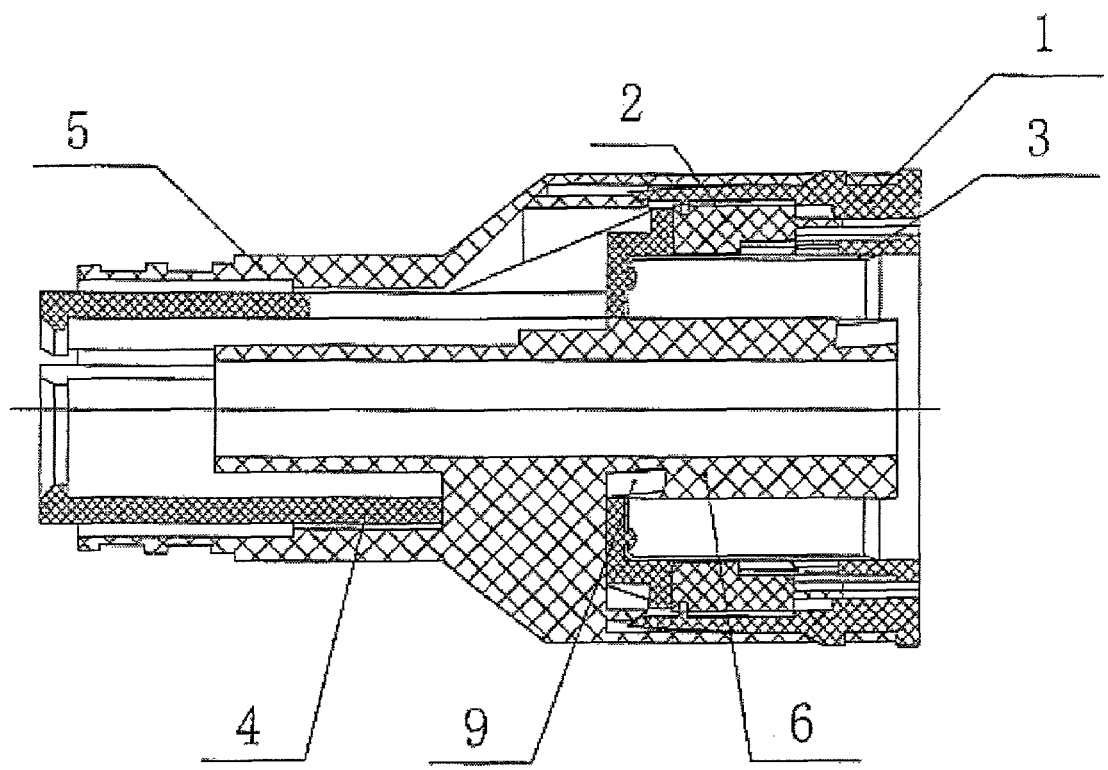
FIG. 9 is a cross-sectional view of a rotatable stapling head with the compression rod driving the scalpel to rotate according to another embodiment of the present invention.
Figure 10:
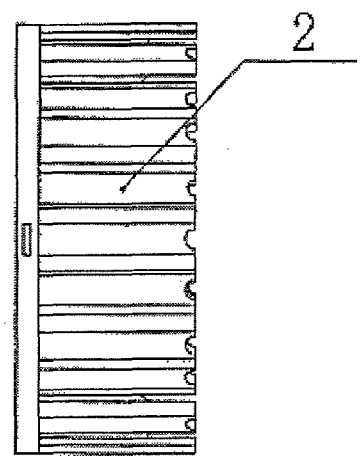
FIG. 10 is a schematic view of the staple driver in the rotatable stapling head as shown in FIG. 9.
Figure 11:
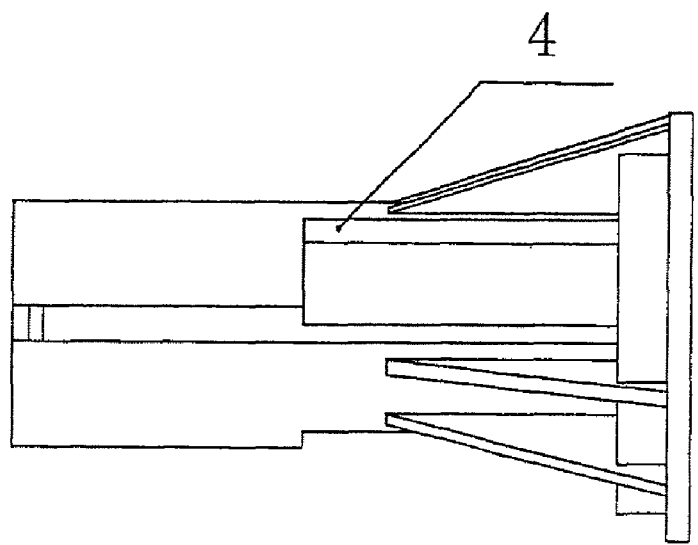
FIG. 11 is a schematic view of the compression rod in the rotatable stapling head as shown in FIG. 9.
Figure 12:
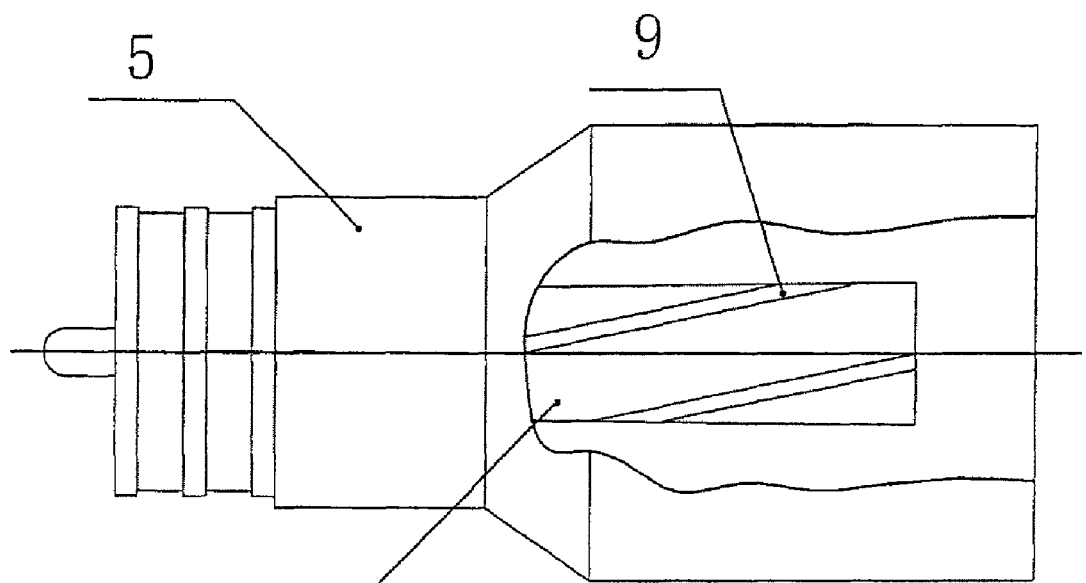
FIG. 12 is a schematic view of the staple casing in the rotatable stapling head as shown in FIG. 9.

As shown in FIG. 6, the staple driver 2 and the compression rod 4 are made integral, the rotating sleeve 7 is disposed at the inner bottom of the annular scalpel; a fixed spiral sleeve 13 is fixed outside the support tube 6, the spiral track 9 is disposed on the outer wall of the fixed spiral sleeve, the support tube 6 has a threaded insert 8 on its front end with a limit fastening nut 10 disposed thereon. A hook 12 is disposed at the bottom of the front cavity of the staple driver 2 so as to hook with the bottom of the rotating sleeve 7. When the staple driver 2 is pushed forward, it drives the rotating sleeve 7 and the scalpel 3 to move forward, meanwhile, the concave-convex structure 11 of the rotating sleeve matches with the spiral track 9 of the fixed spiral sleeve so as to drive the rotating sleeve 7 to rotate. Because the rotating sleeve 7 is riveted with the scalpel 3, the scalpel rotates along with the rotating sleeve 7. After stapling, the scalpel 3 and the rotating sleeve 7 retract back to the staple casing by the force from the hook 12 which is disposed on the staple driver.

Embodiment 4

As shown in FIGS. 9 to 12, the staple driver 2 and the compression rod 4 are disposed separately and smoothly touch each other. When the compression rod 4 is pushed forward, because the spiral track is disposed on the support tube in the staple casing 5, the compression rod 4 rotates while being pushed forward; the scalpel 3 is fixed with the compression rod 4, therefore, the scalpel 3 is driven to move forward while rotating; meanwhile, the staple driver 2 is pushed to move forward but not rotating because it is not connected with the compression rod 4; thus, it enables the stapling head to cut tissue while rotating, therefore the surgery operations are more safe and convenient.

Embodiment 5

Figure 13:
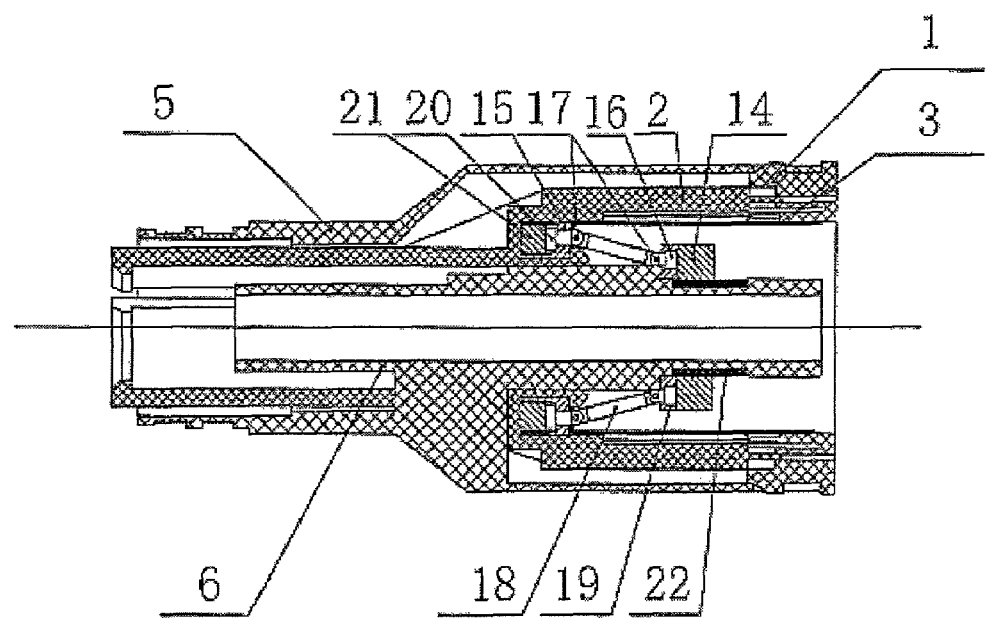
FIG. 13 is a cross-sectional view of a rotatable stapling head employing a connecting rod assembly as its rotating assembly according to another embodiment of the present invention.

As shown in FIG. 13, the rotating assembly of the present invention is a connecting rod assembly; and wherein said staple cartridge 1, staple driver 2, scalpel 3, staple casing 5, and connecting rod assembly constitute a rotating forward mechanism which can rotatably forward said scalpel therein; said staple casing 5 is a tubular casing with an inner step shaped cavity inside which is disposed a support tube 6; a step-shape tubular staple driver 2, which conforms to the shape of the inner wall of the staple casing, is disposed between the support tube 6 and the inner wall of the staple casing; a scalpel cavity is formed in front of the staple casing 5 and the staple driver 2, which matches the annular scalpel 3; the annular scalpel 3 is sleeved outside the support tube 6 and disposed inside the scalpel cavity; and wherein the front circle rim of the staple casing 5 is connected with the annular staple cartridge 1 and the front circle rim of the staple driver 2 contacts with the annular staple cartridge 1; and the annular scalpel 3 is connected with the staple driver 2 and the support tube 6 by means of the connecting rod assembly. The connecting rod assembly comprises a fastening nut 14, a rotating sleeve 15, the first hinge mounts 16, pins 17, connecting rods 18, a hinge mount sleeve 19, the second hinge mounts 20 and a fastening bolt 21; a threaded insert 22 is disposed on a stepped outer wall of the support tube in the annular scalpel 3; the hinge mount sleeve 19 is disposed on a shoulder of the stepped outer wall of the support tube 6 below the threaded insert 22; the first hinge mounts 16 are disposed on the hinge mount sleeve 19; the fastening nut 14 is disposed on the first hinge mounts 16 by means of the threaded insert 22 the bottom of each of the first hinge mounts 16 is connected movably with one end of one of the connecting rod 18 by means of one of the pins 17, the other end of the connecting rod 18 is connected movably with one of the second hinge mounts 20 which is disposed in the rotating sleeve 15 that fixed below the front of the staple driver by means of one of the pins 17. When the staple driver 2 is pushed forward, it drives the scalpel to move forward. Because the front of the connecting rod 18 is fixed, the scalpel 3 moves forward while rotating by the force from the staple driver 2 and the connecting rod 18.

Embodiment 6

As shown in FIGS. 14 to 18, the present invention comprises a staple casing 1, a staple driver 2, a scalpel 3, a staple casing 5 and an inclined surface & rotating sleeve assembly; and wherein said staple cartridge 1, staple driver 2, scalpel 3, staple casing 5, and inclined surface & rotating sleeve assembly constitute a rotating forward mechanism which can rotatably forward said scalpel therein; said staple casing 5 is a tubular casing with an inner step shaped cavity inside which is disposed a support tube 6; a step-shape tubular staple driver 2, which conforms to the shape of the inner wall of the staple casing 5, is disposed between the support tube 6 and the inner wall of the staple casing 5; a scalpel cavity is formed in front of the staple casing 5 and the staple driver 2, which matches the annular scalpel; the annular scalpel 3 is sleeved outside the support tube 6 and disposed inside the scalpel cavity; and wherein the front circle rim of the staple casing 5 is connected with the annular staple cartridge 1 and the front circle rim of the staple driver 2 contacts with the annular staple cartridge 1; and the annular scalpel 3 is connected with the staple driver 2 and the support tube 6 by means of the inclined surface & rotating sleeve assembly. The inclined surface & rotating sleeve assembly comprises a rotating sleeve 24 and a connecting sleeve 23; the connecting sleeve 23 is fixed on the support tube in the staple casing with inclined surfaces 27 disposed on its outer wall; the rotating sleeve 24 is hinged with the annular scalpel 3 with inclined surfaces 28 disposed thereon which match with the inclined surfaces 27 disposed on the connecting sleeve 23; a hook 12 is disposed at the bottom of the front of the staple driver 2 so as to hook with the bottom of the rotating sleeve 24. Said inclined surface & rotating sleeve assembly can be disposed either inside or outside the annular scalpel 3.

Figure 14:
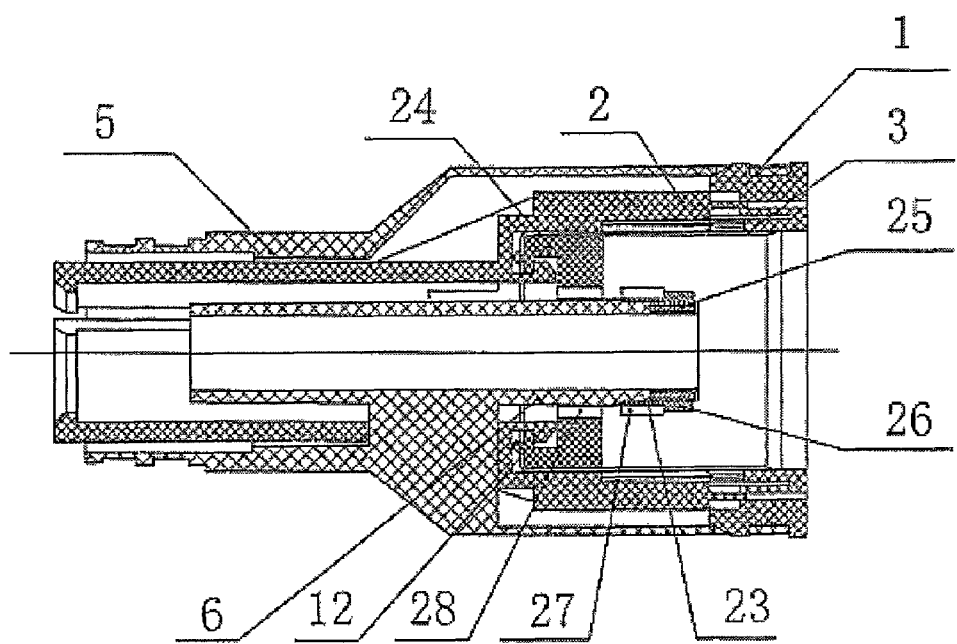
FIG. 14 is a cross-sectional view of a rotatable stapling head employing an inclined surface & rotating sleeve assembly disposed inside the scalpel as its rotating assembly according to another embodiment of the present invention.
Figure 15:
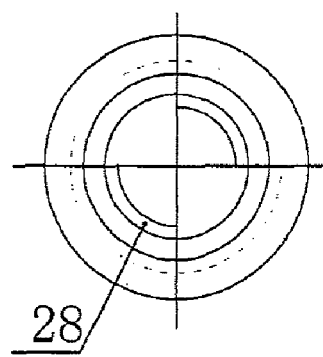
FIG. 15 is a structural view of the rotating sleeve in the rotatable stapling head as shown in FIG. 14.
Figure 16:
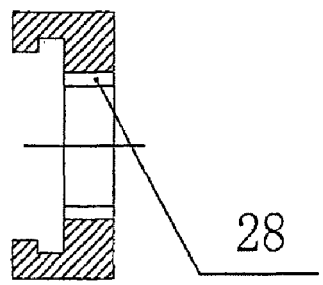
FIG. 16 is a left view of the rotating sleeve as shown in FIG. 15.
Figure 17:
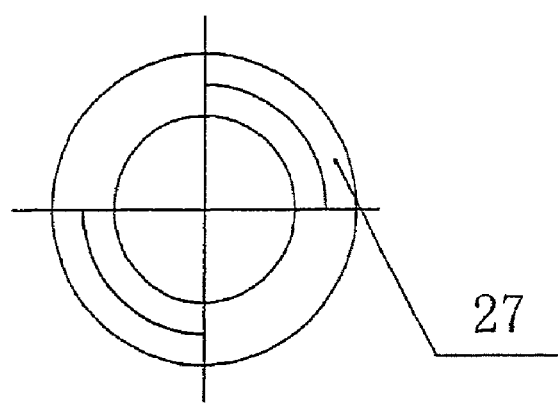
FIG. 17 is a schematic view of the connecting sleeve having inclined surfaces mating with the rotating sleeve in the rotatable stapling head as shown in FIG. 14.

As shown in FIG. 14, when the inclined surface & rotating sleeve assembly is disposed inside the annular scalpel, said inclined surface & rotating sleeve assembly comprises a connecting sleeve 23, a rotating sleeve 24, a threaded insert 25 and a fastening nut 26; the threaded insert 25 is disposed at the front of the support tube 6; the fastening nut 26 is fixed outside the threaded insert 25; inclined surfaces 27 are disposed on the outer wall of the connecting sleeve 23; the rotating sleeve 24 is hinged at the inner bottom of the annular scalpel 3 with inclined surfaces 28 disposed thereon which match with the inclined surfaces 27 disposed on the connecting sleeve 23; a hook 12 disposed at the bottom of the front of the staple driver 2 goes through into the bottom of the annular scalpel 3 so as to hook with the bottom of the rotating sleeve 24, so that the rotating sleeve and the scalpel can be hooked back. In the working state, the staple driver 2 is pushed forward, it drives the scalpel 3 to move forward; when the inclined surfaces 28 of the rotating sleeve 24 matches with the inclined surfaces 27 of the connecting sleeve 23, the rotating sleeve 24 is driven to rotate along with the inclined surfaces. Because the rotating sleeve 24 is riveted with the annular scalpel 3, the scalpel 3 rotates along with the rotating sleeve 24. After stapling, the scalpel 3 and the rotating sleeve 24 retract back to the staple casing 5 by the force from the hook 12 which is disposed on the staple driver 2.

Figure 18:
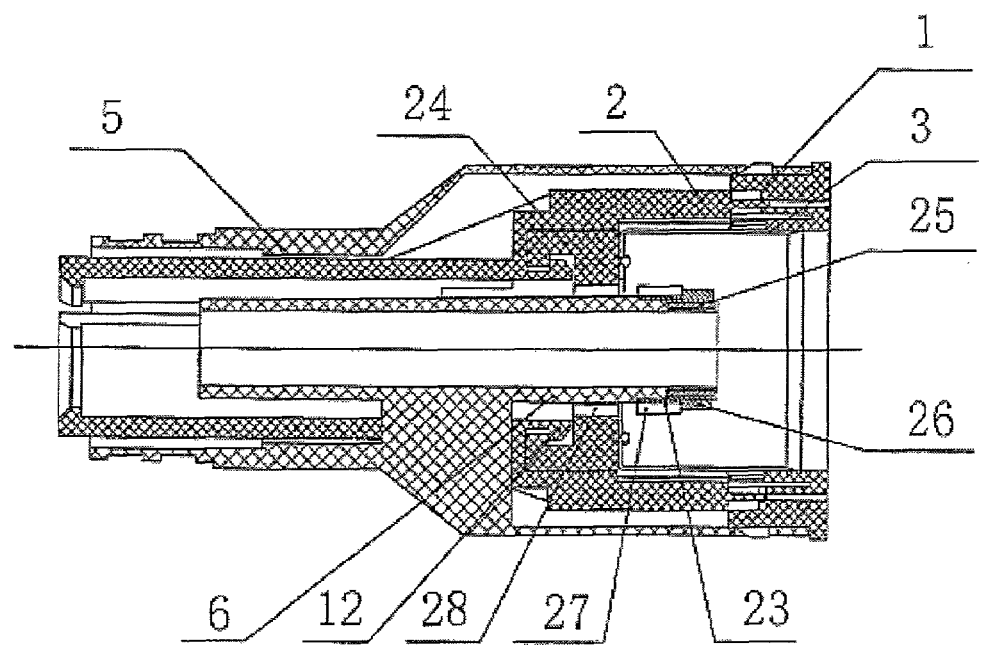
FIG. 18 is a cross-sectional view of a rotatable stapling head employing an inclined surface & rotating sleeve assembly disposed outside the scalpel according to another embodiment of the present invention.

As shown in FIG. 18, when the inclined surface & rotating sleeve assembly is disposed outside the annular scalpel, said inclined surface & rotating sleeve assembly comprises a connecting sleeve 23, a rotating sleeve 24, a threaded insert 25 and a fastening nut 26; the threaded insert 25 is disposed at the front of the support tube 6; the fastening nut 26 is fixed outside the threaded insert 25; inclined surfaces 27 are disposed on the outer wall of the connecting sleeve 23; the rotating sleeve 24 is hinged at the outer bottom of the annular scalpel 3 with inclined surfaces 28 disposed thereon which match with the inclined surfaces 27 disposed on the connecting sleeve 23; a hook 12 is disposed at the bottom of the front of the staple driver 2 so as to hook with the bottom of the rotating sleeve 24. In the working state, the staple driver 2 is pushed forward, it drives the rotating sleeve 24 and the scalpel 3 to move forward; when the inclined surfaces 28 of the rotating sleeve 24 match with the inclined surfaces 27 of the connecting sleeve 23, the rotating sleeve 24 is driven to rotate along with the inclined surfaces. Because the rotating sleeve 24 is riveted with the annular scalpel 3, the scalpel 3 rotates along with the rotating sleeve 24. After stapling, the scalpel 3 and the rotating sleeve 24 retract back to the staple casing 5 by the force from the hook 12 which is disposed on the staple driver 2.

Embodiment 7

Figure 19:
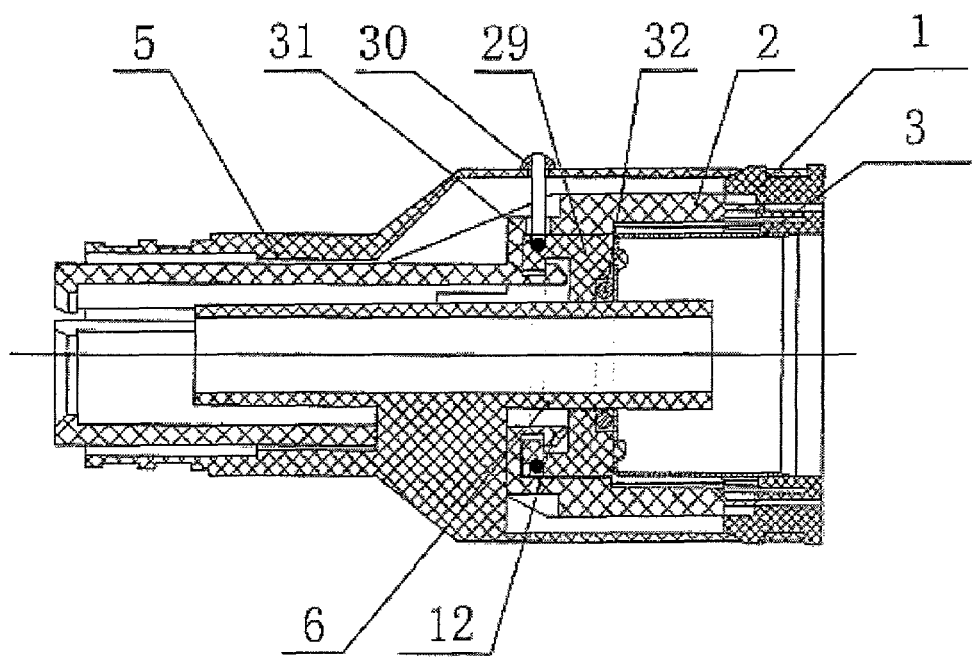
FIG. 19 is a cross-sectional view of a rotatable stapling head employing a string & rotating sleeve assembly as the rotating assembly according to another embodiment of the present invention.

As shown in FIG. 19, the rotating assembly is a string & rotating sleeve assembly; and said string & rotating sleeve assembly comprises a rotating sleeve 29, a string lock 30, a string 31 and a torsion spring 32; the rotating sleeve 29 is sleeved outside the support tube 6 and fixed at the outer bottom of the annular scalpel 3; the upper of the rotating sleeve 29 is connected with the outer wall of the support tube 6 by means of the torsion spring; and the string 31 is disposed below the rotating sleeve 29 with one end of the string 31 fixed at the bottom of the rotating sleeve 29, and the other end of the string goes through out of the staple casing 5 to be fixed with the string lock 30; a hook 12 is disposed at the bottom of the front cavity of the staple driver 2 so as to hook with the bottom of the rotating sleeve 29. When the staple driver 2 is pushed forward, it drives the scalpel 3 to move forward, meanwhile, the rotating sleeve 29 is driven to rotate along with the scalpel 3 because the string is fixed at the bottom of the rotating sleeve and is wound around the outer wall of the rotating sleeve 29. After stapling, the scalpel 3 and the rotating sleeve 29 retract back to the staple casing 5 by the force from the hook 12 which is disposed on the staple driver 2. Accordingly, the string goes to initial state by the force from the torsion spring 32.

Embodiment 8

Figure 20:
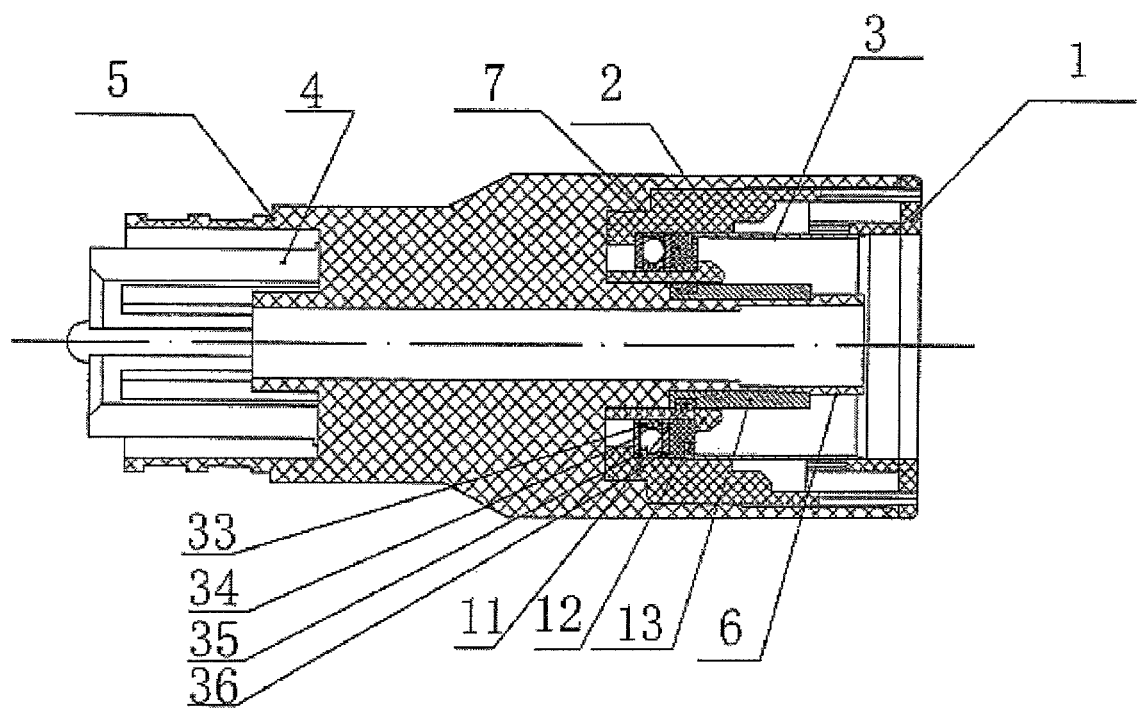
FIG. 20 is a cross-sectional view of a rotatable stapling head employing a rotating sleeve with steps as the rotating assembly according to another embodiment of the present invention.

As shown in FIG. 20, the staple driver 2 and the compression rod 4 are made integral, the annular scalpel 3 as an insert is made integral with the rotating sleeve 7, the fixed spiral sleeve 13 as an insert is made integral with the support tube 6; and gaskets 34 and 36, a ball 35, a ball collar 33 are disposed respectively at the bottom of the rotating sleeve in order, a hook 12 is disposed at the bottom of the front cavity of the staple driver 2 so as to hook with the bottom of the rotating sleeve 7. When the staple driver 2 is pushed forward, it drives the rotating sleeve 7 and the annular scalpel 3 to move forward, meanwhile, the rotating sleeve 7 is driven to rotate because the concave-convex structure 11 of the rotating sleeve 7 matches with the spiral track 9 of the fixed spiral sleeve. The annular scalpel 3 and the rotating sleeve 7 are made integral, therefore, the scalpel rotates along with the rotating sleeve 7. After stapling, the scalpel 3 and the rotating sleeve 7 retract back to the staple casing by the force from the hook 12 which is disposed on the staple driver.

While the above provides a full and complete disclosure of the preferred embodiments of the present invention, various modifications, alternate constructions and equivalents may be employed without departing from the true spirit and scope of the invention. Therefore, the above descriptions and illustrations should not be construed as limiting the scope of the invention, which is defined by the appended claims.

The invention claimed is:

1. A rotatable stapling head of a surgical stapler comprising:
   a staple cartridge, a staple driver, an annular scalpel, a compression rod, a staple casing, and a rotating assembly;
   wherein said staple cartridge, staple driver, annular scalpel, compression rod, staple casing, and rotating assembly constitute a forward-moving and rotating mechanism;
   wherein said rotating assembly includes a rotating sleeve and a spiral track member;
   wherein said staple casing comprises a tubular casing with an inner step shaped cavity inside which is disposed a support tube;
   wherein the staple driver, which conforms to the shape of the inner wall of the staple casing, is disposed between the support tube and the inner wall of the staple casing;
   wherein a scalpel cavity is formed in front of the staple casing and the staple driver, which matches the annular scalpel;
   wherein the annular scalpel is sleeved outside the support tube and disposed inside the scalpel cavity;
   wherein the rotating sleeve has therein a concave-convex structure selected from the group consisting of flutes and bosses;
   wherein the spiral track member is disposed on the support tube inside the staple casing so as to match with the concave-convex structure of the rotating sleeve;
   wherein a front circular rim of the staple casing is connected with the staple cartridge and the front circular rim of the staple driver contacts with the staple cartridge;
   wherein the annular scalpel is connected with the staple driver and the support tube by means of the rotating sleeve; and
   wherein said annular scalpel rotates relative to the staple casing within said forward-moving and rotating mechanism, while said annular scalpel, said staple driver and said compression rod move axially.

2. The rotatable stapling head of a surgical stapler according to claim 1, wherein the rotating sleeve is fixed with the annular scalpel;
   wherein a slide mechanism is disposed at the bottom of the rotating sleeve; and
   wherein a hook is disposed at the bottom of the front cavity of the staple driver so as to hook with the bottom of the rotating sleeve.

3. The rotatable stapling head of a surgical stapler according to claim 2, wherein said slide mechanism comprises balls, ball collars and gaskets.

4. The rotatable stapling head of a surgical stapler according to claim 1, wherein said rotating sleeve is disposed at the inner bottom of the annular scalpel; and
   wherein a hook is disposed at the bottom of the front cavity of the staple driver so as to hook with the bottom of the annular scalpel.

5. The rotatable stapling head of a surgical stapler according to claim 1, wherein said rotating sleeve is disposed at the outer bottom of the annular scalpel; and
   wherein a hook is disposed at the bottom of the front cavity of the staple driver so as to hook with the bottom of the rotating sleeve.

6. The rotatable stapling head of a surgical stapler according to claim 1, wherein the spiral track member is a spiral track directly disposed on the support tube; and
   wherein the rotating sleeve and the support tube are connected by means of the spiral track on the support tube.

7. The rotatable stapling head of a surgical stapler according to claim 1, wherein said spiral track member is a fixed spiral sleeve with the spiral track disposed on the outer wall thereof, and the fixed spiral sleeve is fixed outside the support tube; and
   wherein the support tube has a threaded insert on its front end with a limit fastening nut disposed thereon.

8. The rotatable stapling head of a surgical stapler according to claim 1, wherein said staple driver and the compression rod are disposed separately and smoothly touch with each other.

9. A rotatable stapling head of a surgical stapler comprising: a staple cartridge, a staple driver, an annular scalpel, a compression rod, a staple casing, and a rotating assembly;
   wherein said staple cartridge, staple driver, annular scalpel, compression rod, staple casing, and rotating assembly constitute a forward-moving and rotating mechanism;
   wherein said rotating assembly comprises a connecting rod assembly;
   wherein said staple casing comprises a tubular casing with an inner step shaped cavity inside which is disposed a support tube;
   wherein the staple driver, which conforms to the shape of the inner wall of the staple casing, is disposed between the support tube and the inner wall of the staple casing;
   wherein a scalpel cavity is formed in front of the staple casing and the staple driver, which matches the annular scalpel;
   wherein the annular scalpel is sleeved outside the support tube and disposed inside the scalpel cavity;
   wherein a front circular rim of the staple casing is connected with the staple cartridge and the front circular rim of the staple driver contacts with the staple cartridge;
   wherein the annular scalpel is connected with the staple driver and the support tube by means of the connecting rod assembly; and
   wherein said annular scalpel rotates relative to the staple casing within said forward-moving and rotating mechanism, while said annular scalpel, said staple driver and said compression rod move axially.

10. The rotatable stapling head of a surgical stapler according to claim 9, wherein said connecting rod assembly comprises a fastening nut, a rotating sleeve, first hinge mounts, pins, connecting rods, a hinge mount sleeve, second hinge mounts and a fastening bolt;
    wherein a threaded insert is disposed on a stepped outer wall of the support tube in the annular scalpel;
    wherein the hinge mount sleeve is disposed on a shoulder of the stepped outer wall of the support tube below the threaded insert;
    wherein the first hinge mounts are disposed on the hinge mount sleeve;
    wherein a fastening nut is disposed on the first hinge mounts by means of the threaded insert; and
    wherein the bottom of each of the first hinge mounts is connected movably with one end of one of the connecting rods by means of one of the pins, the other end of the connecting rod is connected movably with one of the second hinge mounts which is disposed in the rotating sleeve that fixed below the front of the staple driver by means of one of the pins.

11. A rotatable stapling head of a surgical stapler comprising a staple cartridge, a staple driver, an annular scalpel, a compression rod, a staple casing, and a rotating assembly;
   wherein said staple cartridge, staple driver, annular scalpel, compression rod, staple casing, and rotating assembly constitute a forward-moving and rotating mechanism;
   wherein said rotating assembly comprises an inclined surface & rotating sleeve assembly;
   wherein said staple casing comprises a tubular casing with an inner step shaped cavity inside which is disposed a support tube;
   wherein the staple driver, which conforms to the shape of the inner wall of the staple casing, is disposed between the support tube and the inner wall of the staple casing;
   wherein a scalpel cavity is formed in front of the staple casing and the staple driver, which matches the annular scalpel;
   wherein the annular scalpel is sleeved outside the support tube and disposed inside the scalpel cavity;
   wherein a front circular rim of the staple casing is connected with the staple cartridge and the front circular rim of the staple driver contacts with the staple cartridge;
   wherein the annular scalpel is connected with the staple driver and the support tube by means of the inclined surface & rotating sleeve assembly; and
   wherein said annular scalpel rotates relative to the staple casing within said forward-moving and rotating mechanism, while said annular scalpel, said staple driver and said compression rod move axially relative.

12. The rotatable stapling head of a surgical stapler according to claim 11, wherein said inclined surface & rotating sleeve assembly comprises a connecting sleeve, a rotating sleeve, a threaded insert and a fastening nut;
   wherein the threaded insert is disposed at the front of the support tube; the connecting sleeve and the fastening nut are fixed respectively outside the threaded insert;
   wherein inclined surfaces are disposed on the outer wall of the connecting sleeve;
   wherein the rotating sleeve is hinged at the inner bottom of the annular scalpel with inclined surfaces disposed thereon which match with the inclined surfaces disposed on the connecting sleeve; and
   wherein a hook disposed at the bottom of the front of the staple driver goes through into the bottom of the annular scalpel so as to hook with the bottom of the rotating sleeve.

13. The rotatable stapling head of a surgical stapler according to claim 11, wherein said inclined surface & rotating sleeve assembly comprises a connecting sleeve, a rotating sleeve, a threaded insert and a fastening nut;
   wherein the threaded insert is disposed at the front of the support tube;
   wherein the connecting sleeve and the fastening nut are fixed respectively outside the threaded insert;
   wherein inclined surfaces are disposed on the outer wall of the connecting sleeve;
   wherein the rotating sleeve is hinged at the outer bottom of the annular scalpel with inclined surfaces disposed thereon which match with the inclined surfaces disposed on the connecting sleeve; and
   wherein a hook is disposed at the bottom of the front of the staple driver so as to hook with the bottom of the rotating sleeve.

14. A rotatable stapling head of a surgical stapler comprising: a staple cartridge, a staple driver, an annular scalpel, a compression rod, a staple casing, and a rotating assembly;
   wherein said staple cartridge, staple driver, annular scalpel, compression rod, staple casing, and rotating assembly constitute a forward-moving and rotating mechanism;
   wherein said rotating assembly comprises a string & rotating sleeve assembly;
   wherein said staple casing comprises a tubular casing with an inner step shaped cavity inside which is disposed a support tube;
   wherein the staple driver, which conforms to the shape of the inner wall of the staple casing, is disposed between the support tube and the inner wall of the staple casing;
   wherein a scalpel cavity is formed in front of the staple casing and the staple driver, which matches the annular scalpel;
   wherein the annular scalpel is sleeved outside the support tube and disposed inside the scalpel cavity;
   wherein a front circular rim of the staple casing is connected with the staple cartridge and the front circular rim of the staple driver contacts with the staple cartridge;
   wherein the annular scalpel is connected with the staple driver and the support tube by means of the string & rotating sleeve assembly; and
   wherein said annular scalpel rotates relative to the staple casing within said forward-moving and rotating mechanism, while said annular scalpel, said staple driver and said compression rod move axially.

15. The rotatable stapling head of a surgical stapler according to claim 14, wherein said the string & rotating sleeve assembly comprises a rotating sleeve, a string lock, a string and a torsion spring;
   wherein the rotating sleeve is sleeved outside the support tube and fixed at the outer bottom of the annular scalpel;
   wherein the upper of the rotating sleeve is connected with the outer wall of the support tube by means of the torsion spring;
   wherein the string is disposed below the rotating sleeve with one end of the string fixed at the bottom of the rotating sleeve, and the other end of the string goes through out of the staple casing to be fixed with the string lock; and
   wherein a hook is disposed at the bottom of the front cavity of the staple driver so as to hook with the bottom of the rotating sleeve.

* * * * *